United States Patent
Canady et al.

(10) Patent No.: US 6,480,111 B2
(45) Date of Patent: Nov. 12, 2002

(54) MOTION DETECTION FOR PHYSIOLOGICAL APPLICATIONS

(75) Inventors: Larry D. Canady, San Antonio, TX (US); Kevin S. Honeyager, San Antonio, TX (US); Jerome A. Helffrich, San Antonio, TX (US); David A. Tong, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/758,840

(22) Filed: Jan. 10, 2001

(65) Prior Publication Data

US 2001/0026222 A1 Oct. 4, 2001

Related U.S. Application Data

(60) Provisional application No. 60/175,186, filed on Jan. 10, 2000.

(51) Int. Cl.[7] .............................................. G08B 23/00
(52) U.S. Cl. ................. 340/573.1; 340/572.2; 340/572.4; 340/572.6; 340/825.36; 340/825.46; 600/534; 600/535; 600/595
(58) Field of Search ........................ 340/573.1, 572.2, 340/572.4, 572.6, 572.7, 582, 825.36, 825.46; 367/185; 128/200.24, 202.13, 920; 600/534, 535, 595

(56) References Cited

U.S. PATENT DOCUMENTS

| 4,267,845 A | 5/1981 | Robertson, Jr. et al. .... 128/721 |
| 4,324,255 A | 4/1982 | Barach et al. ............... 128/630 |
| 4,543,959 A | * 10/1985 | Sepponen .................... 600/440 |
| 4,951,674 A | 8/1990 | Zanakis et al. ......... 128/653 R |
| 4,996,479 A | 2/1991 | Hoenig ........................ 324/248 |
| 5,012,190 A | 4/1991 | Dossel ......................... 324/248 |
| 5,049,818 A | 9/1991 | Doessel et al. .............. 324/248 |
| 5,313,074 A | 5/1994 | Tamura et al. ................. 257/34 |
| 5,360,008 A | * 11/1994 | Campbell, Jr. .............. 600/484 |
| 5,401,530 A | 3/1995 | Tamura et al. ................. 427/63 |
| 5,442,289 A | 8/1995 | Dilorio et al. .............. 324/248 |
| 5,617,856 A | 4/1997 | Tamura et al. ........... 128/653.1 |
| 5,825,293 A | * 10/1998 | Ahmed et al. ............... 340/573 |
| 5,879,297 A | * 3/1999 | Haynor et al. .............. 600/407 |
| 5,902,238 A | * 5/1999 | Golden et al. .............. 600/424 |

OTHER PUBLICATIONS

Ramirez, D., "GMR Sensors Manage Batteries. (Giant Magnetoresistance)", at internet [http://www.findarticles.com/cf_0/mOEDN/18_44/56176670/print.jhtml] dated Sep. 2, 1999, 2 pages, Printed Nov. 16, 2000.

"Magnetic Sensor Products Overview", Honeywell, Inc., at internet [http://www.ssec.honeywell.com/products/magsensor_index.html], 6 pages, Printed Jan. 7, 2000.

"Magnetic Sensors", Honeywell, Inc., at internet [http://www.ssec.honeywell.com/products/magsensor_faq.html], 8 pages, Printed Jan. 7, 2000.

Michael J. Caruso et al., "A New Perspective on Magnetic Field Sensing", p. 1–25, May 1998.

* cited by examiner

Primary Examiner—Jeffery Hofsass
Assistant Examiner—Daniel Previl
(74) Attorney, Agent, or Firm—Baker Botts L.L.P.

(57) ABSTRACT

A method and system for physiological monitoring using a microprocessor-enhanced magnetic field sensor to measure the mechanical effects of body motion is described. The measurements may be used for a variety of applications, such as detection of respiration, cardiac rhythms, and blood pressure. The source or detector may be made sufficiently small so as to be implantable. The system is sufficiently sensitive to provide output data for very small movements.

43 Claims, 2 Drawing Sheets

MOTION DETECTION FOR PHYSIOLOGICAL APPLICATIONS

RELATED PATENT APPLICATION

This application claims the benefit of U.S. Provisional Application No. 60/175,186, filed Jan. 10, 2000 and entitled "System and Method for Motion Detection".

TECHNICAL FIELD OF THE INVENTION

The present invention relates in general to devices for measuring physiological conditions such as respiration and cardiac rhythm, and more specifically, to using magnetic-field-based motion detection for such measurements.

BACKGROUND OF THE INVENTION

Despite the availability of various motion sensors, measurements of physiological functions and conditions has largely been achieved by detecting electrical responses. For example, conventional heart rate monitoring is based on electrocardiograms. As another example, respiration measurement is often achieved with impedance pneumography. Another characteristic of most existing physiological measurement devices is that they require the patient to wear some sort of electrical signal sensor or electrode.

An exception is the breathing monitor disclosed in U.S. Pat. No. 5,825,293, entitled "Apparatus and Method for Monitoring Breathing Magnetically", Ahmed et al. It describes a magnet placed on the patient's chest wall, such that chest wall motion from breathing causes a changing magnetic field at a nearby magnetic field sensor. With suitable analysis, magnetic field variation data can be used to indicate whether or not the patient is breathing.

SUMMARY OF THE INVENTION

One aspect of this invention is a method of measuring mechanical activity associated with physiological motion of a living body. In one embodiment, a magnetic field sensor is placed on an area of the body. The ambient magnetic field is detected by the sensor, with the signal having time varying characteristics representative of the motion. This signal is analyzed to determine characteristics of the motion. Alternatively, a magnet (or magnetized material) rather than the magnetic field sensor may be placed on the body, and a stationary magnetic field sensor used to detect magnetic field changes. The first configuration is useful because it eliminates an additional magnet from the system, but the second may be more sensitive and it rejects external magnetic field variations.

An advantage of the invention is that the sensor system directly measures mechanical effects of motion induced by the body. There is no need to interpret electrical physiological responses.

The system operates without the need for electrical leads or electrodes. All that is required is a magnetic field sensor or magnet (or magnetized material) to be placed in the area of interest; detection is based on magnetic field variations resulting from motion induced in the magnetic field sensor or magnet (or magnetized material) located on the body.

The same sensor system can be used for a variety of applications. In one application, the magnetic field sensor is used to measure respiration. Another application is measurement of cardiac rhythms, from which conditions such as arrhythmia and heartbeat can be detected. Both the respiration and cardiac rhythm applications involve placing the magnetic field sensor (or a magnet or magnetized material), on the patient's torso. A third application, measurement of blood pressure from vein or artery motion, is enabled by analysis of signal amplitude as well as timing. For this application, the magnetic field sensor (or a magnet or magnetized material) is typically placed on the patient's skin over a blood vessel. A fourth application is for motion detection of internally placed catheters or leads associated with various medical devices, and uses a magnetic field sensor (or magnet or magnetized material) placed on the catheter or lead. A fifth application is motion artifact rejection, for example, to eliminate motion-induced noise in a measurement waveform. The magnetic field sensor (or magnet or magnetized material) is placed in the area of interest such that the motion-induced noise is coupled to the magnetic field sensor or magnet. This enables characterization of the noise so that it can be separated from the signal of interest.

The above-described physiological applications require the sensor system to be extremely sensitive. The invention described herein achieves this level of sensitivity. Microprocessor-based nulling techniques result in a system having low power requirements, as well as good resolution despite the presence of ambient magnetic fields, which may be large and time-varying.

A further advantage is that the sensor system can be used to simultaneously measure more than one physiological condition. For example, respiration and cardiac rhythms can be simultaneously measured by using a sensor placed on a patient's chest or abdomen. Also, the magnet may be very small, even to the extent that they may be placed on an eyelid.

DETAILED DESCRIPTION

The following description is directed to various physiological applications of the microprocessor-enhanced magnetic field sensor. These various applications involve measuring some form of motion of a living body. Typically, the applications will be medical applications for human patients. The magnetic field sensor is used to translate mechanical motion associated with the body to an electrical signal.

For these various applications, it should be understood that there are two fundamentally different approaches to operating the magnetic field sensor. In the first approach, changes in the magnetic field of interest can be caused by moving the magnetic field sensor within the ambient (typically static) magnetic field. In the second approach, a stationary magnetic field sensor is used and a magnet (or magnetized material) is moved so as to perturb the magnetic field surrounding the magnetic field sensor. For example, for measurement of respiration, the magnetic field sensor may be placed on the patient's chest and/or abdomen, or a magnet may be placed on the patient's chest and/or abdomen while the magnetic field sensor is located near the patient.

An advantage of the second approach described above is that the magnetic source is sufficiently small so as to be unobtrusively placed on or in the human body. It is also possible that a detection system, which includes the magnetic field sensor, could be made sufficiently lightweight, compact and power-efficient so as to permit placement of the entire system on the patient's body.

Depending on the placement of the magnetic field sensor, it may be used to measure more than one physiological condition. For example, a magnetic field sensor placed on a patient's chest near the sternum can be used to measure respiration and cardiac rhythms. Signal processing techniques, such as filtering or principle component wavelet analysis, can be used to differentiate one source of motion from the other. For example, a heart rate measurement may require more sensitive detection than respiration.

Sensor System Overview

Figure 1:
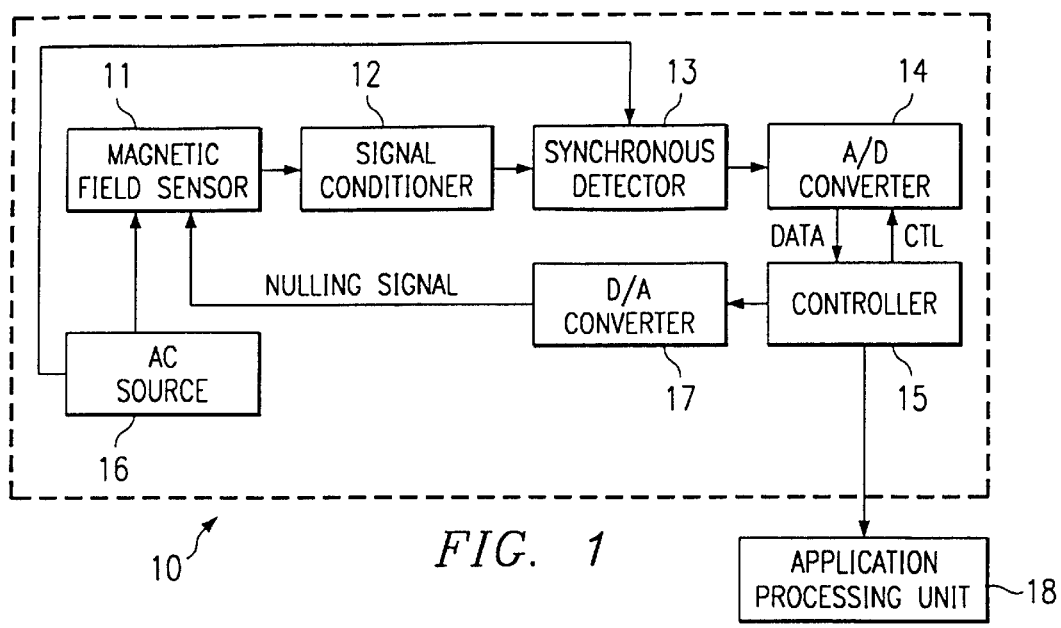
FIG. 1 illustrates a system for detecting physiological motion in accordance with the invention.

FIG. 1 illustrates a magnetic field sensor system 10 in accordance with the invention. As explained below in connection with FIGS. 2–7, various embodiments of the invention use system 10 to acquire different types of physiological data. Each embodiment uses different programming of application processing unit 18 to analyze the signal in a manner appropriate for the measurement of interest.

System 10 essentially comprises a magnetic field sensor 11 followed by signal conditioning circuitry 12, synchronous detector 13, and an analog-to-digital converter (ADC) 14. An AC source 16 is used to excite the magnetic field sensor to enable coherent detection techniques to be used, resulting in enhanced sensitivity and signal-to-noise ratio. A microcontroller 15 handles circuit controls, background nulling, power sequencing, and data processing. Additional circuitry may include a digital-to-analog converter (DAC) 17 to null the large DC offset resulting from the surrounding environment, i.e., the earth's magnetic field.

Depending on the application, sensor 11 is placed in an appropriate location on or inside the patient's body. After a short calibration period, system 10 begins to acquire data by measuring changes in the magnetic field induced by physiological movement associated with that patient.

In the following description, various physiological applications of system 10 are described in terms of the location of the sensor 11. However, it should be understood that alternative embodiments are possible, in which system 10 is made sufficiently small that the entire system 10 can be located on the patient's body, rather than just the magnet (or magnetized material).

If magnetic field sensor 11 is a separate component from system 10, an appropriate link is made to communicate the excitation signal from source 16 to sensor 11 and to communicate the output signal from sensor 11 to signal conditioner 12.

Magnetic Field Sensor

In the example of FIG. 1, magnetic field sensor 11 is sensitive to magnetic fields. One type of commercially available magnetic field sensor is an anisotropic magnetoresistive (AMR) sensor, which consists of magnetically sensitive material whose resistance changes with respect to the magnetic field sensed. A typical AMR sensor is made using semiconductor processing techniques. In one implementation, an AMR sensor comprises four AMR resistors in a Wheatstone-bridge configuration. Two arms of the bridge have magnetically sensitive resistors; the other two resistors are shielded against magnetic fields. When a magnetic field impinges on the sensor, the AMR changes the resistance of the active pair of resistors, and the values of the shielded pair remain constant.

As compared to other magnetic sensors, AMR sensors provide improved sensitivity, power conservation, and temperature stability. They are especially useful for applications that call for small size, simplified designs, and low power-consumption. With sensitivities on the order of tens of microGauss (ten parts per million), AMR sensors may be used to characterize very small changes in a magnetic field.

For purposes of this description, sensor 11 may be described as a "magnetic field sensor". Other types of magnetic field sensors such as fluxgate magnetometers or giant magnetoresistive (GMR) sensors might also be suitable depending upon the application. Sensor 11 may be a single axis sensor, but any number of axes can be implemented by duplicating appropriate circuitry. For example, a single axis sensor placed on a prone patient's chest might measure vertical motion, whereas a two-axis sensor might also detect horizontal motion.

The nature of the physiological applications described herein call for the magnetic field sensor 11 to measure very small changes in the magnetic field in the presence of a large ambient magnetic field. Thus, it is desirable to null the ambient (earth's) field by generating a magnetic field equal to the ambient field, but opposite in direction. The resulting field at the sensor 11, assuming the field is perfectly nulled, is zero Gauss. This special microprocessor-driven nulling circuitry, which uses a coil around each axis of sensor 11, is described below in connection with D/A converter 17.

In alternative embodiments, multiple sensors 11 may be used. For example, the responses from an array of sensors 11 may be used to provide spatial information.

AC Source

In the example of FIG. 1, system 10 uses AC excitation of sensor 11 to improve system sensitivity and signal-to-noise ratio. AC source 16 has a square-wave crystal-controlled oscillator for generating the AC excitation voltage. The frequency of oscillation typically ranges from about 1 kHz to about 200 kHz, depending on the application requirements. Following the crystal oscillator, a bandpass filter produces a sinewave excitation signal.

It is desirable for the amplitude and frequency of excitation signal be stable; variations will introduce changes at the synchronous detector 13 that may result in apparent changes in the detector output signal that are not a result of changes in the magnetic field surrounding the sensor.

The excitation signal stability is desired over the period of time required to make several measurements. For example, when respiration is measured (frequency about 12 times/minute) the stability time period required is about one minute. When heart rate is measured (frequency about 1.5 Hz), the stability time period required is about ten seconds.

Signal Conditioner

Within signal conditioner 12 the output of the magnetic field sensor 11 is first amplified. The output of the amplifier is filtered by second order bandpass filters, centered at the AC source frequency. More than one filter stage may be used for improved filtering capability. The use of more than one stage allows wider component tolerance. For example, two second order stages with a gain of 5 times each will provide fourth-order equivalent filtering with a total gain of about 25 times.

Detector Unit

In the example of FIG. 1, detector unit 13 uses synchronous detection to improve the signal-to-noise ratio of the output signal. Detector circuit 13 also has a lowpass filter, to smooth the output of the synchronous detector. The resulting output is a voltage having an amplitude proportional to the magnetic field amplitude along the sensitive axis of sensor 11.

The combination of synchronous detection and lowpass filtering results in an effective narrow band pass filter with a center frequency equal to the synchronous detector clock frequency and having a bandwidth set by the low pass filter cutoff frequency. Selection of the lowpass filter cutoff frequency depends on the maximum rate of change anticipated for detection by system 10. A typical frequency is 3–35 times the frequency of the expected movement of interest. For example, for respiration and heart rate detection, a typical filter cutoff might be about 7 Hz. This cutoff is lower than that typically used to measure the electrical activity of the heart. However, the mechanical motion induced in the chest wall by the beating heart is naturally low pass filtered, eliminating most of the higher frequency information.

Analog to Digital Converter

Analog to digital converter 14 digitizes the detector output signals. Selection of the resolution and sample rate is application dependent. A high resolution (16 bit or higher) converter may be used to provide micro-Gauss sensitivity.

Controller

Controller 15 controls various aspects of operation of the system. It may be implemented in system 10 as an embedded controller. It may communicate with a separate application processing unit 18, or its functions may be combined with application processing unit 18. Operation of controller 15 for ambient field nulling is described below in connection with D/A converter 17.

Application Processing Unit

Processing unit 18 is programmed with whatever algorithm is appropriate for analyzing the sensor output for the particular physiological application. The analysis may occur in real time, which permits physiological conditions to be monitored. Processing unit 18 may include appropriate memory for programming and data storage. Measurement data may be stored for later review and analysis. Various applications and their methods of signal analysis are described below.

Digital to Analog Converter

As previously mentioned, the ambient (usually the earth's) magnetic field can be offset in order to keep sensor 11 within its linear operating range. In one implementation, a DC current is passed through nulling coils for each axis of sensor 11. This current produces a magnetic field that can be used to oppose the ambient field seen by the sensor 11. The polarity of the nulling field can be inverted by passing current in the opposite direction through the coil windings. This may be accomplished with the aid of software-controlled analog switches. The result, for the circuitry illustrated with a channel gain of approximately 12,500, is an approximate 3–5 mV noise floor, with heart rate signals providing a signal of about 20–30 mV amplitude, and respiration providing a signal of about 100–400 mV amplitude, given the normal range of human body chest wall motion induced by breathing and heart beat activity.

In the example of system 10, the nulling magnetic field is generated by applying a voltage-controlled constant current through the sensor coil(s) (one coil for each axis). For example, a two-axis sensor 11 would have two nulling coils and would use a dual DAC 17. The current is controlled by controller 15. The coils are wound directly onto sensor 11 to optimize power consumption, that is, to reduce the current required to generate the nulling field.

The use of controller 15 and DAC 17 for ambient field nulling is a low power alternative to various other techniques. For example, some GMR and AMR devices are provided with an on-chip nulling terminal. However, these nulling methods may require more power than is desirable for some of the applications described herein.

Physiological Applications

The following description is of various applications of system 10 for measuring motion produced within a living body. For each application, the basic structure of system 10 is the same, except for the programming of application processing unit 18.

Cardiac Rhythm Monitoring

Figure 2:
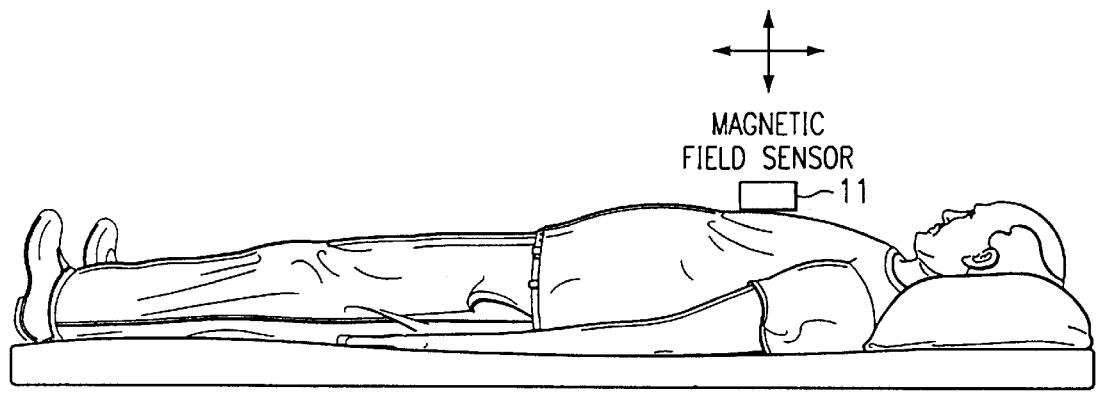
FIGS. 2 and 3 illustrate how the system of FIG. 1 may be used for cardiac rhythm and respiration monitoring.
Figure 3:
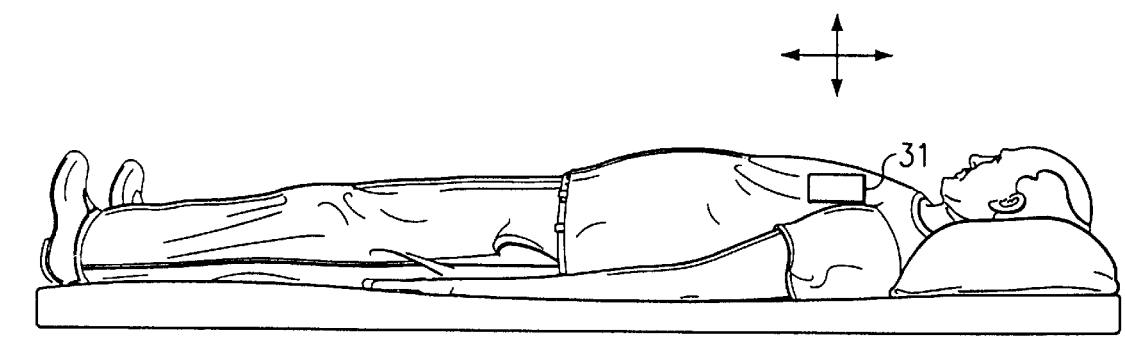

FIGS. 2 and 3 illustrated how system 10 may be used for cardiac rhythm monitoring. For example, conditions such as heart rate or arrhythmia may be detected. The monitoring is "indirect" in the sense that the magnetic field sensor 11 does not make actual contact with the heart. An alternative method of cardiac rhythm monitoring, in which a magnetic field sensor 11 or a magnet (or magnetized material) is placed in leads implanted in the heart, is discussed below in connection with FIGS. 5 and 6.

FIG. 2, the monitoring is accomplished by placing sensor 11 or the entire system 10 in contact with the patient. In FIG. 3, the monitoring is performed by placing a magnet (or magnetized material) 31 on the patient's body and locating magnetic field sensor 11 sufficiently close to the patient. Typically, contact with the patient will be on the chest wall or abdomen while the patient is lying prone. In this manner, system 10 measures the patient's chest wall motion resulting from respiration and the beating heart.

Although the various applications described below are explicitly directed to placement of a sensor, it should be understood, that for each application, a magnetized material could be substituted for the sensor and the detection performed by a nearby sensor.

Respiration Monitoring

In a manner similar to cardiac rhythm monitoring, respiration may be monitored by either placing the magnetic field sensor 11 (or a magnet or magnetized material) in proximate contact with the patient's torso, such as on the chest wall or abdomen. Such measurements are able to detect conditions indicating sleep apnea or sudden infant death syndrome (SIDS).

As the patient breathes, chest and abdominal motion is induced. Changes in the magnetic field generated by the motion can be measured with the magnetic field sensor 11.

Blood Pressure Monitoring

For blood pressure monitoring, a magnetic field sensor 11 is placed on a blood vessel, typically by placing it on the skin over a vessel that is close to the skin. The magnetic field sensor 11 moves in response to the patient's pulse. The amplitude of the output signal can be analyzed to indicate blood pressure. For example, a magnetic field sensor 11 placed on the carotid vessel will produce a signal whose timing is indicative of pulse and whose amplitude and shape is indicative of blood pressure. For blood pressure measurement, some means for attaching the magnetic field sensor 11 securely to the skin, such as a strap or tape, may improve accuracy.

Catheter and Lead Motion Detection

Figure 4:
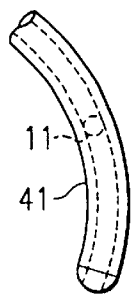
FIG. 4 illustrates how the system of FIG. 1 may be used for lead motion detection.
Figure 4:
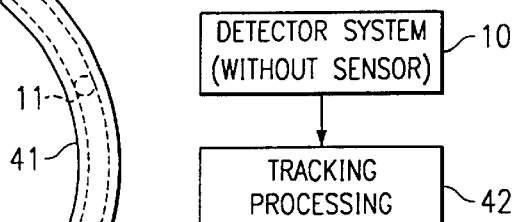

FIG. 4 illustrates how system 10 may be used for catheter and lead motion detection. In this application, the objective is to detect motion of various types of catheters and leads, generally referred to as "leads" 41, which may be located inside the body. Often such leads are used in connection with medical devices, such as pacemakers and defibrillators. Magnetic field sensor 11 is placed on, or implanted in, or otherwise affixed to, the lead 41. Using magnetic field sensor 11, system 10 measures the motion of the lead 41 and its orientation in one or more directions. System 10 thereby provides navigation and location capabilities for motion associated with the lead. The sensor 11 may be placed at the tip of the lead or at any point along the lead. Multiple sensors 11 could be placed along the lead to measure motion at each sensor location.

In a variation of the application of FIG. 4, analogous to the embodiment of FIG. 3, a magnet (or magnetized material) may be affixed to the lead. For this embodiment, detector system 10 would contain a magnetic field sensor.

Figure 5:
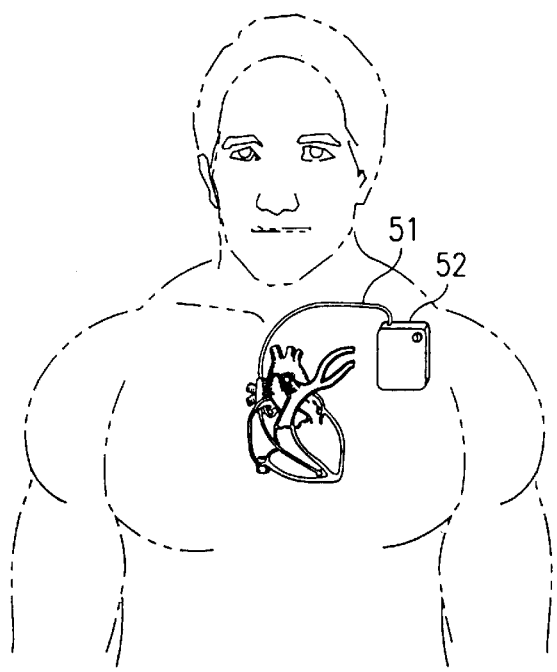
FIG. 5 illustrates how a magnet may be placed on, or implanted in, leads implanted in chambers of the heart for an implantable cardioverter defibrillator (ICD).

FIG. 5 illustrates how a magnetic field sensor 11 could be affixed to leads 51 that are implanted in heart chambers. These leads 51 are especially useful in connection with implantable cardioverter defibrillators (ICDs) 52, which are devices implanted in the chest of a patient to monitor and treat potentially life threatening cardiac arrhythmias. They are typically implanted on the left side of the body and rest on the musculature covering the rib cage. ICD 52 uses the electrical signals obtained from leads 51 to monitor cardiac rhythm. A magnetic field sensor 11 in conjunction with system 10 detects heart wall motion that is coupled to the ICD lead 51 attached to the heart muscle. More than one lead 51 may be used. For example, a first lead 51 might lead to the atria and a second lead 51 to the ventricle.

Like other applications of the invention described herein, the embodiment of FIG. 5 may be modified in a manner analogous to the embodiment of FIG. 3. Thus, a magnetic or magnetized material, may be placed in the lead, rather than the sensor. The sensor would then be located in ICD 52.

Figure 6:
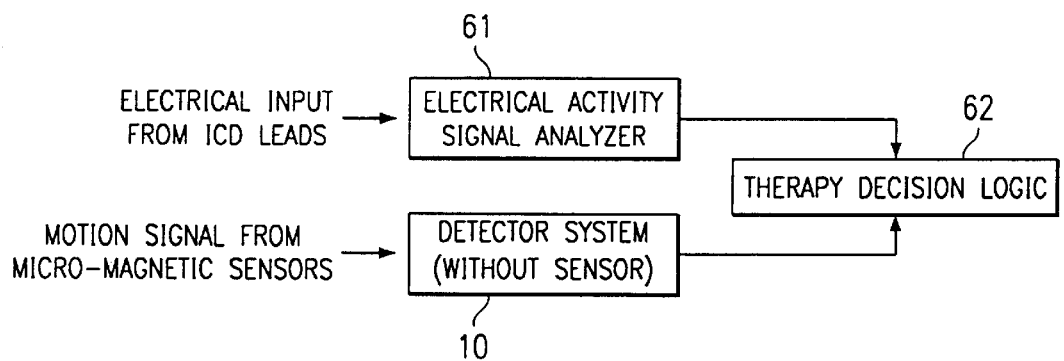
FIG. 6 illustrates how an ICD may be improved by using motion data supplied by the system of FIG. 1.

FIG. 6 illustrates how ICD algorithms may be used to monitor the wall motion signals obtained by leads 51, in conjunction with the electrical signals to detect cardiac arrhythmias. The signals from magnetic field sensor(s) 11 affixed to leads 51 are obtained and processed by system 10. Electrical signals from leads 51 are processed by a signal analyzer 61. Application processing unit 62 may also be used discriminate between different cardiac arrhythmias, such as normal sinus rhythm, ventricular fibrillation, ventricular tachycardia, arterial fibrillation, and arterial tachycardia.

In a related application, sensor 11 could be attached to another sensor to measure motion of the second sensor. For example, sensor 11 could be attached to an ECG electrode.

Motion Artifact Reduction

Figure 7:
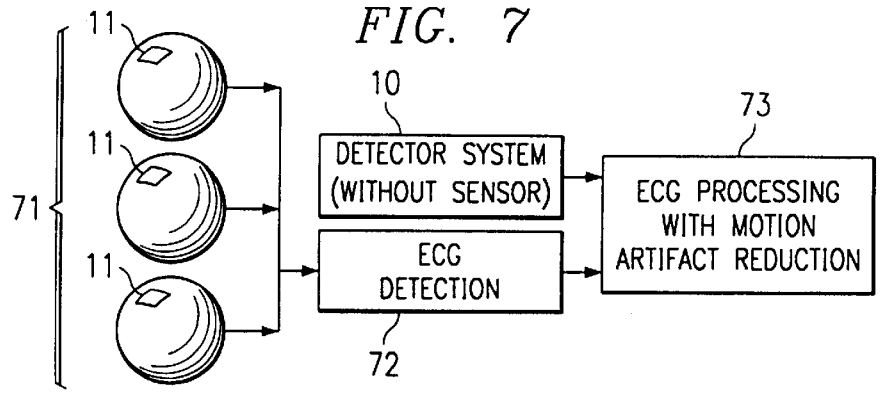
FIG. 7 illustrates how the system of FIG. 1 may be used for motion artifact reduction, to reduce noise in signals acquired by an ECG device.

FIG. 7 illustrates how system 10 may be used for motion artifact reduction, that is, to detect and algorithmically reduce motion artifacts in signals acquired by various medical devices. Often, when such devices are in use, electrode or patient movement, or both, produce motion artifacts, which can produce large amplitude noise signals in the signal of interest. In some scenarios, these motion artifacts can result in misdiagnosis or lead to mistreatment of a medical condition.

In the example of system 10, electrodes 71 are in place for an ECG (electrocardiogram) system 72. It is assumed that noise in the ECG signal has been introduced as a result of motion of electrodes 71. A magnetic field sensor 11 is affixed to each electrode 71. The signal from the magnetic field sensors 11 is detected and conditioned by system 10, then analyzed in real time by processing unit 73 to detect changes in that signal that indicate motion artifacts. At the same time, an ECG signal from electrodes 71 is detected and conditioned by ECG detection unit 72. Once the motion artifact signal is identified, processing unit 73 filters the motion artifact signal from the ECG signal.

Another example of a device that might use system 10 for noise reduction is a probe such as is used by pulse oximeters to detect blood saturation levels.

In a manner analogous to the embodiment of FIG. 3, a magnet or magnetized material, may be affixed to the electrodes, rather than the sensor. In this case, the detector system 10 would include the sensor.

Operation

In operation, system 10 is used to measure an amplitude and a frequency of movement within a magnetic field of the earth using a system located proximate to the patient. The system 10 (or magnetic field sensor 11 or a magnet (or magnetized material) 31 moves with the patient or with an object in or on the human body. The AC source 16 provides an oscillator signal output operating at a preselected frequency of oscillation. Magnetic field sensor 11 detects the magnetic field along one or more axes and provides an electrical output signal proportional to the magnetic field of the earth along each axis at the moving magnetic field sensor location. The output signal is filtered to provide a filtered output signal, such as by using a bandpass filter having a center frequency approximately equal to the frequency of oscillation. Detector 13 detects the filtered output signal at approximately the frequency of oscillation and filters the signal to provide a demodulated signal having a frequency that is equal to the frequency of movement, and an amplitude approximately proportional to the amplitude of the movement.

OTHER EMBODIMENTS

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the scope of the invention as set forth and defined by the following claims.

What is claimed is:

1. A method of measuring mechanical activity associated with physiological motion of a living body, comprising the steps of:

locating at least one magnetic field sensor on or in an area of the body, such that the sensor measures magnetic field changes caused by motion of that area of the body relative to an ambient magnetic field;

detecting a signal from the sensor, the signal having time varying characteristics representative of the motion; and analyzing the signal to determine characteristics of the motion as indicated by the signal.

2. The method of claim 1, further comprising the step of nulling the ambient magnetic field.

3. The method of claim 2, wherein the magnetic field sensor has at least one axis and the nulling is performed by passing current through a coil wound around each axis of the magnetic field sensor.

4. The method of claim 2, wherein the nulling is performed by using a processor to calculate the value of a nulling current to be applied to a nulling coil resulting in a magnetic field substantially equal and opposite to that of the magnetic field to be nulled.

5. The method of claim 1, wherein the magnetic field sensor measures motion along a single axis.

6. The method of claim 1, wherein the magnetic field sensor measures motion along multiple axes.

7. The method of claim 1, wherein the locating step is performed by locating the magnetic field sensor on the torso and the analyzing step determines chest wall motion induced by respiration.

8. The method of claim 1, wherein the locating step is performed by locating the magnetic field sensor on the torso and the analyzing step determines chest wall motion induced by the heart.

9. The method of claim 1, wherein the locating step is performed by locating the magnetic field sensor on the skin over a blood vessel.

10. The method of claim 1, wherein the locating step is performed by affixing the magnetic field sensor to a lead within the body.

11. The method of claim 1, further comprising the step of using motion data provided by the analyzing step to eliminate motion artifacts in a signal acquired by another measurement device.

12. The method of claim 1, wherein the signal represents more than one physiological motion, and further comprising the step of filtering the signal to differentiate between multiple types of motion.

13. The method of claim 1, wherein the multiple types of motion are motion induced by respiration and motion induced by the heart.

14. The method of claim 1, further comprising the step of analyzing the signal to determine the intensity of the motion.

15. The method of claim 1, wherein the magnetic field sensor is magnetoresistive sensor.

16. The method of claim 1, wherein the locating step is performed by placing signal detection circuitry on the body in a unit also containing the magnetic field sensor.

17. The method of claim 1, wherein the locating step is performed by locating multiple sensors.

18. The method of claim 17, wherein the multiple sensors form an array and wherein the analyzing step provides spatial data.

19. The method of claim 1, wherein the locating step is performed by affixing the sensor to a different type of sensor.

20. A method of measuring mechanical activity associated with a physiological motion of a living body, comprising the steps of:

locating a magnetized material on or in an area of the body;

sensing the magnetic field resulting from the motion of the magnetized material, using a magnetic field sensor;

nulling the ambient magnetic field surrounding the body, by generating a nulling magnetic field in the area of the sensor and that is sensed by the sensor, the nulling magnetic field being substantially equal and opposite to that of the ambient magnetic field;

detecting a signal from the magnetic field sensor, the signal having time varying characteristics representative of the motion; and analyzing the signal to determine characteristics of the motion as indicated by the signal.

21. The method of claim 20, wherein the magnetic field sensor has at least one axis, and the nulling is performed by passing current through a coil wound around each axis of the magnetic field sensor to generate a magnetic field that is substantially equal and opposite to that of the ambient magnetic field to be nulled.

22. The method of claim 20, wherein the magnetic field sensor measures motion along a single axis.

23. The method of claim 20, wherein the magnetic field sensor measures motion along multiple axes.

24. The method of claim 20, wherein the locating step is performed by locating the magnetized material on the torso and the analyzing step determines motion induced by respiration.

25. The method of claim 20, wherein the locating step is performed by locating the magnetized material on the torso and the analyzing step determines motion induced by the heart.

26. The method of claim 20, wherein the locating step is performed by locating the magnetized material on the skin over a blood vessel to measure motion induced by blood flowing through the vessel.

27. The method of claim 20, wherein the locating step is performed by affixing the magnetized material to a lead within the body.

28. The method of claim 20, further comprising the step of using motion data provided by the analyzing step to eliminate motion artifacts in a signal acquired by another measurement device.

29. The method of claim 20, wherein the signal represents more than one physiological motion, and further comprising the step of filtering the signal to differentiate between these two types of motion.

30. The method of claim 20, wherein the multiple types of motion are motion induced by respiration and motion induced by the heart.

31. The method of claim 20, further comprising the step of analyzing the signal to determine the intensity of the motion.

32. The method of claim 20, wherein the magnetic field sensor is magnetoresistive sensor.

33. The method of claim 20, wherein the nulling is performed by calculating the value of a nulling current to be applied to a nulling coil resulting in a magnetic field substantially equal and opposite to that of the ambient magnetic field to be nulled.

34. A method of measuring mechanical activity associated with a physiological motion of a living body, comprising the steps of:

locating a magnetized material on the skin over a blood vessel;

sensing the magnetic field resulting from the motion of the magnetized material, using a magnetic field sensor;

detecting a signal from the magnetic field sensor, the signal having time varying characteristics representative of the motion;

analyzing the signal to determine characteristics of the motion as indicated by the signal and nulling the ambient magnetic field surrounding the body, by generating a nulling magnetic field in the area of the sensor, the nulling magnetic field being substantially equal and opposite to that of the ambient magnetic field.

35. A method of measuring mechanical activity associated with a physiological motion of a living body, comprising the steps of:

affixing a magnetized material to a lead implanted in the body;

sensing the magnetic field resulting from the motion of the magnetized material, using a magnetic field sensor;

nulling the magnetic field surrounding the body, by generating a nulling magnetic field in the area of the sensor and that is sensed by the sensor, the nulling magnetic field being substantially equal and opposite that of the ambient magnetic field;

detecting a signal from the magnetic field sensor, the signal having time varying characteristics representative of the motion;

analyzing the signal to determine characteristics of the motion as indicated by the signal.

36. A method of measuring mechanical activity of the heart associated with a physiological motion of the heart, comprising the steps of:

locating a magnetized material over the heart;

sensing the magnetic field resulting from the motion of the magnetized material, using a magnetic field sensor;

detecting a signal from the magnetic field sensor, the signal having time varying characteristics representative of the motion;

analyzing the signal to determine heart motion as indicated by the signal.

37. The method of claim 36, further comprising the step of nulling the ambient magnetic field surrounding the body, by generating a nulling magnetic field in the area of the sensor, the nulling magnetic field being substantially equal and opposite to that of the ambient magnetic field.

38. A sensor system for measuring motion associated with a living body, comprising:

a magnetic field sensor, the magnetic field sensor having a nulling coil;

an AC excitation source for providing an excitation signal to the magnetic field sensor;

a signal conditioning circuit for amplifying a signal provided by the magnetic field sensor;

a detection unit for demodulating the filtered signal from the signal conditioning circuit;

an analog to digital converter for converting the demodulated signal to a digital signal;

a controller for calculating a nulling signal value; and a digital to analog converter for providing a nulling signal to the nulling coil.

39. The sensor system of claim 38, wherein the magnetic field sensor is magnetoresistive sensor.

40. The sensor system of claim 38, wherein the controller provides a voltage controlled constant current signal.

41. The sensor system of claim 38, wherein the detection unit provides synchronous detection using a signal provided by the AC excitation source.

42. The sensor system of claim 38, wherein the magnetic field sensor is in the same housing as the rest of the system elements.

43. The sensor system of claim 38 wherein the magnetic field sensor is remote from the rest of the system elements.

* * * * *